United States Patent [19]

Boigegrain et al.

[11] Patent Number: 5,198,586

[45] Date of Patent: Mar. 30, 1993

[54] PROCESS FOR THE PREPARATION OF PHENYLETHANOLAMINOTETRALINS

[75] Inventors: Robert Boigegrain, Castelnau le Lez, France; Roberto Cecchi, Lodi-Milan; Sergio Boveri, Tortona, both of Italy

[73] Assignee: Sanofi, Paris, France

[21] Appl. No.: 603,247

[22] Filed: Oct. 25, 1990

Related U.S. Application Data

[63] Continuation of Ser. No. 231,374, Aug. 11, 1988, abandoned.

[30] Foreign Application Priority Data

| Aug. 12, 1987 | [FR] | France | 87 11497 |
| Mar. 30, 1988 | [FR] | France | 88 04219 |
| Jun. 14, 1988 | [FR] | France | 88 07947 |

[51] Int. Cl.$^5$ ............................................. C07C 213/00
[52] U.S. Cl. ............................. 564/356; 560/45; 562/455; 564/139; 564/170; 564/357; 564/363; 564/365
[58] Field of Search ............... 564/170, 356, 357, 363, 564/139, 365; 560/45; 562/455

[56] References Cited

U.S. PATENT DOCUMENTS

| 3,048,633 | 8/1962 | Russell et al. | 564/356 X |
| 3,300,532 | 1/1967 | Zellner | 564/170 X |
| 3,536,712 | 10/1970 | Keck et al. | 564/356 X |
| 3,574,211 | 4/1971 | Keck et al. | 564/356 X |
| 3,804,834 | 4/1974 | Menthrup et al. | 564/356 X |
| 3,954,871 | 5/1976 | Buu-Hoi et al. | 564/356 X |
| 4,329,358 | 5/1982 | Ainsworth et al. | 564/165 |
| 4,707,497 | 11/1987 | Cecchi et al. | 564/308 |
| 4,886,914 | 12/1989 | Castro et al. | 564/402 |

FOREIGN PATENT DOCUMENTS

| 0211721 | 2/1987 | European Pat. Off. |
| 0253257 | 1/1988 | European Pat. Off. |
| 2803582 | 8/1979 | Fed. Rep. of Germany |

OTHER PUBLICATIONS

March, *Advanced Organic Chemistry, etc.*, 3rd Ed. John Wiley and Sons, New York (1985) pp. 702–707, 1099, and 1100.

*Primary Examiner*—Richard L. Raymond
*Assistant Examiner*—P. O'Sullivan
*Attorney, Agent, or Firm*—Bacon & Thomas

[57] ABSTRACT

A process for the preparation of phenylethanolaminotetralins of formula

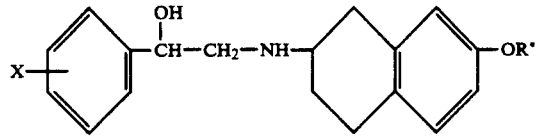

wherein X is hydrogen, a halogen, a trifluoromethyl or a lower alkyl group and R° is hydrogen or a methyl group substituted by a carboxy or a lower carbalkoxy group, which comprises treating a mandelic acid with a 2-amino-7-hydroxytetralin, optionally alkylating with a lower alkyl haloacetate and reducing the amido group of the mandelamide into a methyleneamino group. The mandelamides intermediates are novel.

9 Claims, No Drawings

PROCESS FOR THE PREPARATION OF PHENYLETHANOLAMINOTETRALINS

This application is a continuation of application Ser. No. 07/231,374 filed Aug. 11, 1988, now abandoned.

The present invention provides a process for the preparation of phenylethanolaminotetralins, more particularly by amidation of a mandelic acid with an aminotetralin and by reduction, and the intermediates used in this process.

The European patent Specification 211721 discloses phenylethanolaminotetralins of formula

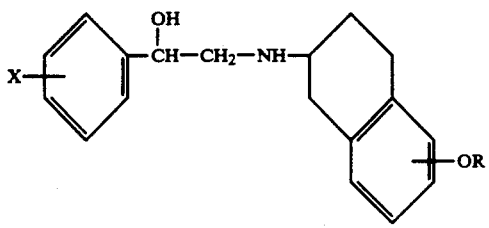

wherein X is hydrogen, halogen, a trifluoromethyl group or a lower alkyl group and R is hydrogen; a lower alkyl group unsubstituted or substituted by a cycloalkyl group of from 3 to 7 carbon atoms, a hydroxy group, a lower alkoxy, carboxy or lower carbalkoxy group; a cycloalkyl group of from 3 to 7 carbon atoms; or a lower alkanoyl group and their pharmaceutically acceptable salts.

According to this document, the compounds of formula (A) and their pharmaceutically acceptable salts have interesting pharmacological properties, the compounds bearing the OR substituent in 7 position of the tetralin ring having revealed a particularly marked lipolytic activity.

In the present description:
the term "lower alkyl", designates a monovalent radical of a saturated hydrocarbon containing from 1 to 4 carbon atoms, such as methyl, ethyl, propyl, isopropyl or n-butyl;
the term "lower carbalkoxy", designates the carboxyl group esterified with a lower alkyl as defined hereinabove;
the term "halogen" includes the four halogens fluorine, chlorine, bromine, iodine, the first three being particularly preferred;
the terms "tetralin" and "tetralone" are referred to 1,2,3,4-tetrahydronaphtalene.

According to the above European Patent Specification, the products of formula (A) are prepared following different preparative methods that always involve a reaction of a 2-aminotetralin or a 2-oxotetralin with
a phenylethanolamine or
an epoxystyrene or
a phenylglyoxal or
an alpha-haloacetophenone.

Among the preparative methods of the products of formula (A) hereinabove, an O-alkylation is described that, starting from 2-[(7-hydroxy-1,2,3,4-tetrahydronaphth-2-yl)amino]-1-phenylethanol or from 2-[(7-hydroxy-1,2,3,4-tetrahydronaphth-2-yl)amino]-1-(3-chlorophenyl)ethanol, by reaction with ethyl bromoacetate gives the 2-[(7-carbethoxymethoxy-1,2,3,4-tetrahydronaphth-2-yl)-amino]-1-phenylethanol or the 2-[(7-carbethoxymethoxy-1,2,3,4-tetrahydronaphth-2-yl)-amino]-1-(3-chlorophenyl)ethanol. This reaction does not actually give good results because the yield in end product is very low.

Still according to the above European Patent Specification, the products of formula (A) may be prepared as diastereoisomers or optically pure stereoisomers by using one or the two starting compounds in an optically active form. However, the obtention of optically active stereoisomers generally involves further crystallizations of the final product that lower the yields and, above all, a hard practical work.

It has now been found that if a 2-amino-7-hydroxytetralin is reacted with a mandelic acid, there is obtained an amide as a mixture of racemates that are in diastereoisomeric relationship each other and that may be easily separated.

It has also been found that the amides thus obtained may be reduced in order to obtain the phenylethanolaminotetralins without any interference with the stereochemistry of the products.

It has further been found that starting from a racemic aminotetralin and from an optically active mandelic acid, or vice-versa, there is obtained an amide a mixture of diastereoisomers easily detectable and separable by chromatography that, after separation, give optically pure phenylethanolaminotetralins by reduction.

It has finally been found that amides prepared by reaction of a mandelic acid with a 2-amino-7-hydroxytetralin may be O-alkylated by a lower alkyl haloacetate in very good yields and that the product thus obtained may be reduced in order to prepare the corresponding O-carbalkoxymethylphenylethanolaminotetralin in a global yield higher than that of the O-alkylation described in EP 211 721.

Thus, the present invention provides a process for the preparation of phenylethanolaminotetralins of formula

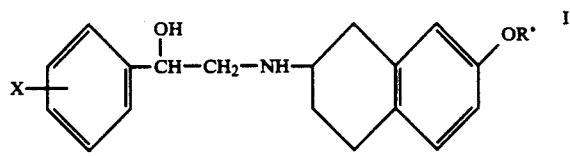

wherein X is as defined hereinabove and R* is hydrogen or a methyl group substituted by a carboxy or a lower carbalkoxy group, and of their pharmaceutically acceptable salts, which comprises reacting a functional derivative of a mandelic acid of formula

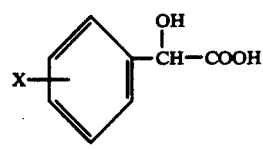

wherein X is as defined hereinabove, with an aminotetralin of formula

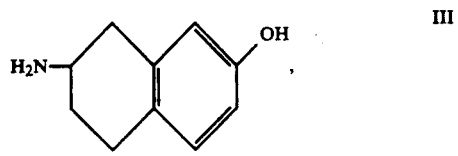

the mandelamine thus obtained of formula

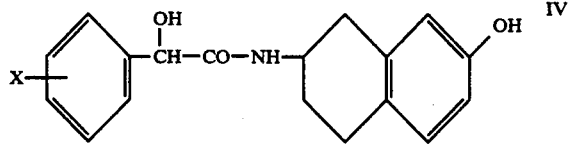

wherein X is as defined hereinabove, is then, submitted to a reduction for the transformation of the amido group into the methyleneamino group or alternatively treated with a lower alkyl haloacetate in the presence of a basic condensation agent, the above mentioned haloacetate being a bromo-, chloro- or iodoacetate; on this second assumption submitting the resulting product, in any order to a reduction for the transformation of the amido group into a methylene amino group and, if desired, to a saponification of the lower carbalkoxy group into the carboxy group; and, if desired, transforming the product thus obtained into one of its pharmaceutically acceptables salts.

Among the compounds that may be prepared following the process of the present invention, those of formula I wherein X is as defined hereinabove and R° is hydrogen or a carbethoxymethyl group are particularly preferred.

The chloride, the anhydride, a mixed anhydride, an active ester or a free acid suitably activated, for example, with dicyclohexylcarbodiimide or with hexafluorophosphate of benzotriazolyl-N-oxytris(dimethylamino)-phosphonium (BOP) may be used as a functional derivative. A mandelic acid activated with a condensing agent such as BOP is preferably used as a starting compound.

The reaction of the functional derivative of mandelic acid with the 2-amino-7-hydroxytetralin of formula III hereinabove is carried out in an organic solvent such as methylene chloride, optionally in the presence of a proton acceptor such as triethylamine.

Preferably, an equimolecular amount of mandelic acid, BOP and aminotetralin is used.

Thus, the corresponding mandelamide of formula IV is obtained that is isolated and, if desired, separed into its diastereoisomers. This separation is carried out by chromatography and each stereoisomer thus separated may be used for the following step.

Thus, starting from a racemic mandelic acid (II) and from a racemic 2-amino-7-hydroxytetralin (III), a mixture of mandelamide diastereoisomers is obtained that, by separation, gives the couple of RR,SS and RS,SR diastereoisomers.

Starting, for example, from an optically active mandelic acid and from a racemic (III) aminotetralin, there is obtained a mandelamide of formula IV as a couple of (RR+RS) or (SS+SR) diastereoisomers that, after separation, gives the (RR) and (RS) or (SS) and (SR) pure enantiomers.

A (R)-mandelic acid is used as advantageous starting product, preferably the (R)-3-chloromandelic acid. The racemic 3-chloromandelic acid can also be used.

If the starting mandelic acid is in racemic form, the aminotetralin of formula III will be preferably used in optically active form.

Particularly preferred aminotetralins are
(R)-2-amino-7-hydroxy-1,2,3,4-tetrahydronaphtalene
and
(S)-2-amino-7-hydroxy-1,2,3,4-tetrahydronaphtalene.

A racemic 2-amino-7-hydroxy-1,2,3,4-tetrahydronaphtalene can also be used.

The mandelamide of formula IV may be directly submitted to a reduction for the transformation of the amido group into the methyleneamino group; alternatively the mandelamine is treated with a lower alkyl haloacetate in alkaline medium. The O-alkylation reaction is carried out according to the known techniques using a lower alkyl chloro- acetate, bromoacetate or iodoacetate, the bromoacetate being preferred. An alkali metal hydroxide or carbonate, for example potassium carbonate, may be used as an alkaline condensing agent and the reaction may be carried in the presence of a catalytic agent such as potassium iodide. The (lower carbalkoxy)methyl ether of the amide IV is isolated in very good yields according to the conventional techniques.

The product thus obtained may be directly submitted to a reduction of the amido group into a methyleneamino group, or it may be saponified in order to transform the lower carbalkoxy group into the free or salified carboxy group according to well known techniques.

Thus, the reduction of the amido group into the methyleneamino group may be carried out on a mandelamide of formula

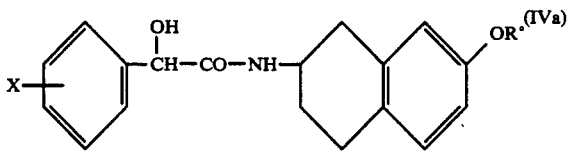

wherein X and R° are as defined hereinabove.

The reduction step of the mandelamide of formula IVa is carried out, for example, by action of an hydride, such as lithium aluminium hydride or of diborane, more particularly by action of a reagent generating diborane such as the complex between borane and dimethylsulfide, hereinafter designated "borane-methylsulfide". The reaction is carried out in an organic solvent, such as tetrahydrofuran and the compound of formula I is isolated according to the known techniques.

In case of reduction of a mandelamide of formula IVa wherein R° is a methyl substituted by an optionally salified carboxy group or, more particularly, by a lower carbalkoxy group, this group may be also reduced into the alcohol. Thus, in this case, the use of a reducing reagent that allows to obtain, at least preferably, the selective reduction of the amido group, is preferred. In any case, more particularly when a mandelamide of formula IVa, wherein R° is a methyl substituted by a carbalkoxy group, is reduced, there is obtained a mixture of the product of formula I wherein R° is a methyl substituted by the corresponding lower carbalkoxy group and of a product of formula

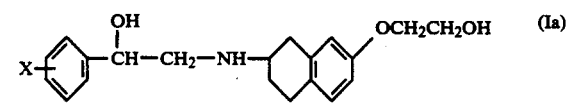

wherein X is as defined hereinabove.

The products of formula Ia are novel and have a good activity on the intestinal motility.

If borane-methylsulfide is used as reducing agent and the reaction is carried out at low temperature (15°-25° C.) the reduction of the amido group is preferably obtained and the corresponding compound of formula I, wherein R° is a lower carbalkoxy or carboxy substituted methyl group, is obtained in global yields higher than those described in EP 211 721.

The reduction reaction respects the stereochemistry of the mandelamide IVa and the products of formula I may be thus obtained as a racemic mixture or as diastereoisomers or optically pure isomers starting from the appropriate mandelamide.

The 2-amino-7-hydroxytetralin of formula III is prepared starting from the corresponding methoxytetralone of formula

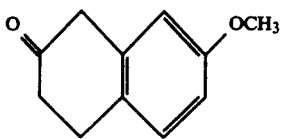

V by reaction with benzylamine, reduction of the resulting benzylimine by sodium borohydride, debenzylation by catalytic hydrogenation and demethylation by 48% hydrobromic acid.

The two optically active forms of the aminotetralins of formula III are prepared by resolution of the racemates according to known methods, for example by salification with an optically active acid, preferably mandelic acid.

The mandelamides of formula IVa hereinabove are novel and represent the key intermediates of the process of the present invention.

Thus, it is another object of the present invention to provide compounds of formula IVa, in racemic form or in form of their separated stereoisomers.

The following examples illustrate the invention without, however, limiting it. The specific optical rotation symbol is indicated as [alpha], but it must be read [alpha]$_D^{20}$.

PREPARATION I 2-amino-7-hydroxytetralin hydrobromide; SR 58518 A (a) A mixture of 8 g of 7-methoxy-2-tetralone, 4.8 g of benzylamine, 150 ml of anhydrous toluene and 100 mg of p.toluenesulfonic acid is heated with reflux. The residual oil is evaporated to dryness, taken up with 100 ml of methanol then 8.5 g of sodium borohydride are carefully added to the solution at 0°-5° C. The mixture is left under stirring at room temperature overnight, then 50 ml of water are added thereto. The solution is left under stirring for 30 minutes, the solvent is evaporated, the residue is taken up with 30 ml of water and 10 ml of a concentrated ammonium hydroxide solution. The product is extracted with 200 ml of ethyl acetate, the organic phase is dried over sodium sulfate, filtered and evaporated to dryness. A dark oil is obtained that is purified by flash chromatography (elution with a 95/5 mixture of ethyl acetate/methanol). The base thus obtained is transformed into its hydrochloride by dissolving it in 40 ml of isopropanol and by adding isopropanol saturated with hydrogen chloride. Thus, there is obtained 11.4 g of 7-methoxy-2-benzylamino-1,2,3,4-tetrahydronaphtalene hydrochloride; m.p. 265°-267° C. (dec.).

(b) The above product, dissolved in 200 ml of methanol and 100 ml of water, is submitted to a hydrogenation in presence of 1.2 g of 10% palladium charcoal, under atmospheric pressure at 45°-50° C. After 4 hours the mixture is filtered, evaporated to dryness, taken up twice with absolute ethanol and evaporated to dryness. A white solid is obtained that is taken up with 70 ml of isopropanol in the warm. By cooling, the resulting suspension precipitates and gives 7.8 g of 2-amino-7-methoxytetralin hydrochloride; m.p. 214°-216° C.

(c) An amount of 6.6 g of the above product is suspended in 80 ml of 48% hydrobromic acid and the mixture is heated with reflux for 2 hours. The solution is evaporated to dryness, then the residue is taken up with absolute ethanol and evaporated to dryness twice. Thus, an oil is obtained that is dissolved in 20 ml of isopropanol in the warm. By addition of 30 ml of ethyl ether to the solution, there is obtained 6.8 g of crystalline 2-amino-7-hydroxytetralin hydrobromide; m.p. 171°-173° C.

PREPARATION II

R(+)-2-amino-7-hydroxytetralin monohydrate; SR 58554

To a solution in 550 ml of absolute ethanol of 50 g of 2-amino-7-methoxytetralin as a raw base, obtained from the corresponding hydrochloride (PREPARATION I b) by neutralisation with 10% sodium hydroxide, extraction with ethyl acetate and evaporation of the solvent, there is added a solution of 43 g of (+) mandelic acid in 550 ml of absolute ethanol. After a night at room temperature, the precipitate which forms is filtered and crystallized twice from absolute ethanol, recovering each time the crystallized product after standing overnight at room temperature. Thus there is obtained 34.2 g (74%) of the pure salt of (+)mandelic acid with the (+)-2-amino-7-methoxytetralin; m.p. 190°-192° C. The mother-liquors of this first crystallization are separated and used for PREPARATION III hereinbelow. An amount of 34 g of the salt thus obtained is suspended in 300 ml of water and the reaction mixture is made alkaline with N sodium hydroxide. The base is extracted with ethyl acetate, the solution is evaporated to dryness and the residue is taken up with 260 ml of 48% hydrobromic acid. The reaction mixture is heated with reflux for 3 hours, evaporated to dryness under reduced pressure and the residue thus obtained is taken up with 70 ml of water. The aqueous solution is made alkaline with concentrated ammonium hydroxide, cooled overnight and filtered. Thus, there is obtained 17 g of R(+)-2-amino-7-hydroxytetralin as a monohydrate; SR 58554; m.p. 143°-144° C., [alpha]=+85.1° (methanol, c=0.5%). The hydrochloride of this product has a rotatory power corresponding to that of the literature (Molecular Pharmacology 1982, 22, 281-289).

PREPARATION III

S(−)-2-amino-7-hydroxytetralin monohydrate, SR 58555

The separated mother-liquors of the first crystallization of the product SR 58554 (PREPARATION II) are evaporated to dryness, the residue thus obtained is suspended in 300 ml of water and the mixture is made alkaline with N sodium hydroxide. The base is extracted with ethyl acetate. By operating as described in PREPARATION II and by using the base thus obtained and (−)mandelic acid as starting products, there is obtained the salt of (−)mandelic acid with (−)-2-amino-7-methoxytetralin (m.p. 189°–191° C.) that, by treatment with N sodium hydroxide, gives 17 g of S(−)-2-amino-7-hydroxytetralin as a monohydrate; SR 58555; m.p. 143°–144° C., [alpha]=−86.9° (methanol, c=0.5%). The hydrochloride of this product has a rotatory power corresponding to that of the literature (Molecular Pharmacology 1982, 22, 281-289).

EXAMPLE 1

(a)

N-(7-hydroxy-1,2,3,4-tetrahydronaphth-2-yl)-3-chloromandelamide, SR 58534 (mixture of diastereoisomers)

To a suspension of 6.5 g of 2-amino-7-hydroxytetralin hydrobromide (PREPARATION Ic), 4.98 g of 3-chloromandelic acid and 10.69 g of benzotriazolyl-N-oxytris-(dimethylamino)phosphonium hexafluorophosphate (BOP) in 120 ml of methylene chloride, there is added 7.44 ml of triethylamine slowly and the reaction mixture is left to react under stirring at room temperature. After 3 hours, 100 ml of a saturated sodium chloride solution are added and the mixture is left under stirring for 30 minutes at room temperature. A volume of 200 ml of ethyl acetate is added and the two phases are separated. The organic phase is washed with a solution of 2N hydrochloric acid, then with a saturated sodium bicarbonate solution and then with a saturated sodium chloride solution. The organic phase is dried over sodium sulfate and concentrated under reduced pressure. There is obtained 12 g of a brown impure oil which is detected by thin layer chromatography (TLC). The oil is purified by flash chromatography (elution with a 6/4 mixture of ethyl acetate/cyclohexane) and all of the fractions are collected. There is obtained 7.5 g (84%) of a chromatographically (TLC) pure pale yellow oil, that solidifies at the pump and is triturated with ether.

(b)

(RS,SR)-N-(7-hydroxy-1,2,3,4-tetrahydronaphth-2-yl)-3-chloromandelamide, SR 58535 (less polar diastereoisomer)

An amount of 6 g of the diastereoisomeric mixture SR 58534, obtained as described hereinabove, is dissolved in the warm in 80 ml of ethyl ether. After a night in the refrigerator, a precipitate is obtained that is filtered. There is obtained 1.4 g of a white solid, that in TLC (elution with a 1/1 mixture of ethyl acetate/cyclohexane), corresponds to the less polar spot of the two spots of the mixture SR 58534. The mother-liquors are submitted to a flash chromatography (elution with 1/1 mixture of ethyl acetate/cyclohexane). An amount of 1.2 g of a solid product corresponding to the less polar product spot, 1.8 g of the mixture and 1.9 g of the product corresponding to the more polar product spot, are obtained. An amount of 2.6 g of the product corresponding to the less polar isomer is crystallized in 60 ml of ethyl acetate to obtain 2.1 g of the first pure isomer; m.p. 172°–174° C.

(c)

(RR,SS)-N-(7-hydroxy-1,2,3,4-tetrahydronaphth-2-yl)-3-chloromandelamide, SR 58536 (more polar diastereoisomer)

The more polar isomer obtained as described in (b), SR 58536, is a white oil which, in TLC, has the same shift that the (RR) isomer, SR 58533, described in Example 20 hereinbelow. The oil thus obtained (1.9 g), dissolved in a mixture of 15 ml of ethyl acetate and of 5 ml of ethyl ether is left at room temperature for 48 hours, to obtain the crystalline SR 58536; m.p. 136°–138° C.

EXAMPLE 2

N-(7-hydroxy-1,2,3,4-tetrahydronaphth-2-yl)-4-chloromandelamide

To a mixture of 3.2 g of 2-amino-7-hydroxytetralin hydrobromide (PREPARATION Ic), 2.4 g of 4-chloromandelic acid and 5.2 g of benzotriazolyl-N-oxytris-(dimethylamino) phosphonium hexafluorophosphate in 50 ml of methylene chloride, there is added 3.6 ml of triethylamine. The solution obtained is left under stirring at room temperature for 3 hours, then a saturated sodium chloride solution is added and the mixture is stirred for 30 minutes. The organic phase that separates is evaporated to dryness and an oil is obtained that is dissolved in 200 ml of ethyl acetate. The solution thus obtained is washed twice with 40 ml of a 2N hydrochloric acid, twice with a saturated sodium bicarbonate solution and, then, with a saturated sodium chloride solution. The solution is dried over sodium sulfate, filtered and evaporated to dryness. The oil so obtained is chromatographed (elution with a 1/1 mixture of ethyl acetate/cyclohexane) and all of the fractions are collected. An amount of 2.7 g (63%) of N-(7-hydroxy-1,2,3,4-tetrahydronaphth-2-yl)-4-chloromandelamide is obtained as a diastereoisomeric mixture; m.p. about 170° C. (large interval of melting), pure enough for a further reaction. In this mixture, the (RS,SR) and (RR,SS) diastereoisomers are well detectable by chromatography; they are easily separable and obtainable in pure form.

EXAMPLE 3

(a) Mixture of stereoisomers

N-[(2R)-7-hydroxy-1,2,3,4-tetrahydronaphth-2-yl]-(R)-mandelamide, and

N-[(2S)-7-hydroxy-1,2,3,4-tetrahydronaphth-2-yl]-(R)-mandelamide, SR 58542

To a solution of 10 g of 2-amino-7-hydroxytetralin hydrobromide (PREPARATION Ic), 6.3 g of (R)-mandelic acid and 16 g of BOP in 200 ml of anhydrous methylene chloride, there is added 8.1 g of triethylamine slowly and the solution thus obtained is stirred at room temperature for 3 hours. A volume of 100 ml of a saturated sodium chloride solution is added, the reaction mixture is stirred at room temperature for 30 minutes, then 400 ml of ethyl acetate are added, the phases are separated and the aqueous phase is eliminated. The organic phase is washed twice with 50 ml of 2N hydrochloric acid, twice with a saturated sodium bicarbonate solution and, then, the solution is dried over sodium sulfate, filtered and evaporated to dryness. The oil so obtained is purified by flash chromatography (elution with a 6/4 mixture of ethyl acetate/cyclohexane) and all of the fractions are collected. An amount of 10.5 g (yield 88%) of mandelamide SR 58542 is obtained as a thick oil that, which in TCL, appears to be constituted by the two diastereoisomers, the percent of which has not been determined.

(b) N-[(2R or 2S)-7-hydroxy-1,2,3,4-tetrahydronaphth-2-yl](R)-mandelamide, SR 58543, less polar isomer An amount of 10.5 g of mixture of diastereoisomers SR 58542, obtained as described hereinabove, is divided in three portions of about 3 g. Each portion is submitted to a flash chromatography (elution with a 1/1 mixture of ethyl acetate/cyclohexane). The fractions, obtained from the three chromatographies, are collected to give 3.1 g of an oil corresponding to the less polar spot, 3.2 g of a solid corresponding to the more polar spot and 2 g of a mixture of the two products. An amount of 3.1 g of the less polar isomer is treated at the mechanical pump and a vitreous solid having an undefined melting point is obtained; [alpha]= −107° (methanol, c=0.5%). Yield of the separation of the mixture: 30%. After 24 hours at room temperature, the vitreous solid crystallizes; it is taken up with ethyl ether and filtered; m.p. 157°-159° C. The [alpha] is unchanged.

(c) N-[(2S or 2R)-7-hydroxy-1,2,3,4-tetrahydronaphth-2-yl]-(R)-mandelamide, SR 58544, more polar isomer An amount of 3.2 g of a white solid corresponding to the more polar isomer, obtained as described in (b), is crystallized from 20 ml of ethyl acetate to give 2.8 g of SR 58544; m.p. 145°-147° C.; [alpha]= +26° (methanol, c=1%).

EXAMPLE 4

N-(7-hydroxy-1,2,3,4-tetrahydronaphth-2-yl)-2-(3-chlorophenyl)-2-hydroxyethanamine, SR 58339, mixture of diastereoisomers To a suspension of 0.9 g of lithium aluminium hydride in 20 ml of anhydrous tetrahydrofuran, there is slowly added a solution of 1.8 g of the N-(7-hydroxy-1,2,3,4-tetrahydronaphth-2yl)-3-chloromandelamide described in Example 1 (a) (SR 58534) in 30 ml of tetrahydrofuran. The reaction mixture is heated with reflux for 4 hours, cooled with an ice-and-water bath, treated with 2 ml of water, 2 ml of a concentrated sodium hydroxide solution and 10 ml of water again. The mixture is stirred at room temperature for 20 minutes, then 50 ml of ethyl acetate are added thereto. The mixture is filtered on CELITE (registered TRADEMARK) to break the emulsion. The organic phase which separates is dried over sodium sulfate, filtered and evaporated to dryness. There is obtained 1.2 g of an oil that is purified by flash chromatography (elution with a 9/1 mixture of methylene chloride/methanol). The purified base is dissolved in 10 ml of ethyl acetate and, by cooling, 0.35 g of SR 58339 base is obtained; m.p. 133°-138° C.; undefined percent of the diastereoisomers. In this mixture, the (RS,SR) and (RR,SS) diastereoisomers are not detectable by chromatography and they may be separated by other techniques only.

Its hydrochloride, SR 58339A, is described in Example 8 of the European patent 211721.

EXAMPLE 5

(RS,SR)-N-(7-hydroxy-1,2,3,4-tetrahydronaphth-2-yl)-2-(3-chlorophenyl)-2-hydroxyethanamine, SR 58523

To a solution of 6 g of SR 58535, obtained as described in Example 1 (b), in 60 ml of anhydrous tetrahydrofuran, heated with reflux under nitrogen stream, there is added, during 20 minutes, 4.5 ml of a 10M solution of the borane-methylsulfide complex, diluted in 20 ml of anhydrous tetrahydrofuran. After adding dropwise of 40 ml of methanol, the mixture is heated at reflux for other 30 minutes, then evaporated to dryness, taken up with 30 ml of water, 5 ml of concentrated ammonium hydroxide and 200 ml of ethyl acetate. The organic phase is separated, dried over sodium sulfate and evaporated to dryness. The residue is sumbitted to a flash chromatography (elution with a 9/1 mixture of methylene chloride/methanol). By crystallization of the solid residue in 50 ml of ethyl acetate, 1.2 g of product melting at 180°-184° C. is obtained, that, after recrystallization from 60 ml of ethyl acetate, gives pure SR 58523; m.p. 184°-186° C.

EXAMPLE 6

(RR,SS)-2-[(7-hydroxy-1,2,3,4-tetrahydronaphth-2-yl)amino]-2-(3-chlorophenyl)-2-hydroxyethanamine, SR 58524

By operating as described in Example 5, starting from 4 g of SR 58536 obtained as described in Example 1(c), 2.4 g of pure SR 58524, crystallized from isopropanol, are obtained; m.p. 143°-145° C.

EXAMPLE 7

N-(7-hydroxy-1,2,3,4-tetrahydronaphth-2-yl)-2-(4-chlorophenyl)-2-hydroxyethanamine, SR 58521, mixture of diastereoisomers To a suspension of 0.9 g of lithium aluminium hydride in 20 ml of anhydrous tetrahydrofurane there is added, during 10 minutes under nitrogen stream, a solution of 2.2 g of diastereoisomeric mixture of N-(7-hydroxy-1,2,3,4-tetrahydronaphth-2-yl)-4-chloromandelamide, as obtained in Example 2, in 30 ml of anhydrous tetrahydrofuran. The reaction mixture is heated with reflux for 3 hours, then 0.45 g of lithium aluminium hydride is added thereto and the mixture thus obtained is heated with reflux for 90 minutes. To the mixture cooled at 5° C., there is added 50 ml of ethyl ether, and, then, 20 ml of water dropwise. The solution is extracted with 100 ml of ethyl acetate, the organic phase is separated, dried over sodium sulfate, filtered and evaporated to dryness. An oil is obtained that is purified by flash chromatography (elution with a 85/15 mixture of methylene chloride/methanol). A solid product in obtained that, crystallized from 20 ml of ethyl acetate, gives 0.7 g of the SR 58521 as a diastereoisomeric mixture; m.p. 152°-156° C. (yield 33%). In this mixture, the (RS,SR) and (RR,SS) diastereoisomers are not detectable by chromatography and they can be separated by other techniques only.

EXAMPLE 8

(a) To a solution of 7 g of R(+)-2-amino-7-hydroxy-1,2,3,4-tetrahydronaphtalene monohydrate (PREPARATION II), 7.2 g of racemic 3-chloromandelic acid, 16 g of BOP in 200 ml of anhydrous methylene chloride, there is added 3.9 g of triethylamine slowly and the solution thus obtained is stirred at room temperature for 3 hours. A volume of 100 ml of a saturated sodium chloride solution is added. The mixture is stirred at room temperature for 30 minutes and 400 ml of ethyl acetate are added thereto. The phases thus obtained are separated and the aqueous phase is eliminated. The organic phase is washed twice with 50 ml of 2N hydrochloric acid, then twice with a saturated sodium bicarbonate solution and, then, the organic phase is dried over sodium sulfate, filtered and evaporated to dryness.

The product thus obtained is purified by flash chromatography (elution with a 6/4 mixture of ethyl acetate/cyclohexane) and all of the fractions are collected to give the N-[(2R)-7-hydroxy-1,2,3,4-tetrahydronaphth-2-yl]-(RS)-3-chloromandelamide as diastereoisomeric mixture.

(b) An amount of 15 g of the above diastereoisomeric mixture, is submitted to a flash chromatography (elution with a 1/1 mixture of ethyl acetate/cyclohexane). An amount of 4.5 g of a product corresponding to the less polar spot, 5 g of a product corresponding to the more polar spot and 3 g of a mixture of the two products is obtained. An amount of 4.5 g of the less polar isomer is treated at the mechanical pump to obtain the N-[(2R)-7-hydroxy-1,2,3,4-tetrahydronaphth-2-yl]-(S)-3-chloromandelamide, SR 58588, as a solid having an undefined melting point; [alpha]= +92.5° (methanol, c=1%).

(c) An amount of 5 g of the white solid corresponding to the more polar isomer obtained as described in (b), crystallized from 20 ml of ethyl acetate, gives 4.3 g of N-[(2R)-7-hydroxy-1,2,3,4-tetrahydronaphth-2-yl]-(R)-3-chloromandelamide, SR 58533; m.p. 143°–147° C.; [alpha]= +35.1° (methanol, c=1%).

EXAMPLE 9

By operating as described in Example 8 and substituting the S(−)-2-amino-7-hydroxy-1,2,3,4-tetrahydronaphtalene monohydrate (PREPARATION III), for the R(+)-2-amino-7-hydroxy-1,2,3,4-tetrahydronaphtalene monohydrate there is obtained:
(a) N-[(2S)-7-hydroxy-1,2,3,4-tetrahydronaphth-2-yl]-(RS)-3-chloromandelamide, as a mixture of diastereoisomers;
(b) N-[(2S)-7-hydroxy-1,2,3,4-tetrahydronaphth-2-yl]-(R)-3-chloromandelamide, SR 58587; less polar isomer; undefined melting point; [alpha]= −95° (methanol, c=1%);
(c) -[(2S)-7-hydroxy-1,2,3,4-tetrahydronaphth-2-yl]-(S)-3-chloromandelamide, SR 58574; m.p. 145°–146° C.; more polar isomer; [alpha]= −34.2° (methanol, c=1%).

EXAMPLE 10

(a) To a solution of 7.0 g of R(+)-2-amino-7-hydroxy-1,2,3,4-tetrahydronaphtalene monohydrate (PREPARATION II), 5.8 g of racemic mandelic acid, 15.3 g of BOP in 200 ml of anhydrous methylene chloride there is added 3.9 g of triethylamine slowly and the solution thus obtained is stirred at room temperature for 3 hours. A volume of 100 ml of a saturated sodium chloride solution is added. The mixture is stirred for 30 minutes at room temperature and 400 ml of ethyl acetate are added thereto. The phases thus obtained are separated and the aqueous phase is eliminated. The organic phase is washed twice with 50 ml of 2N hydrochloric acid, then twice with a saturated sodium bicarbonate solution and, then, the organic phase is dried over sodium sulfate, filtered and evaporated to dryness. The product thus obtained is purified by flash chromatography (elution with a 6/4 mixture of ethyl acetate/cyclohexane) and all of the fractions are collected to give the N-[(2R)-7-hydroxy-1,2,3,4-tetrahydronaphth-2-yl]-(RS)-mandelamide as diastereoisomeric mixture.

(b) An amount of 12 g of the above diastereoisomeric mixture is submitted to a flash chromatography (elution with a 1/1 mixture of ethyl acetate/cyclohexane). There is obtained 4 g of a product corresponding to the less polar spot, 4.5 g of a product corresponding to the more polar spot and 2 g of a mixture of the two products. An amount of 4 g of the less polar isomer is treated at the mechanical pump to obtain the N-[(2R)-7-hydroxy-1,2,3,4-tetrahydronaphth-2-yl]-(S or R)-mandelamide, SR 58561; m.p. 159°–160° C.; [alpha]= +110° (methanol, c=0.5%).

(c) An amount of 4.5 g of the white solid corresponding to the more polar isomer obtained as described in (b) is crystallized from 20 ml of ethyl acetate. There is obtained 3.9 g of N-[(2R)-7-hydroxy-1,2,3,4-tetrahydronaphth-2-yl]-(R or S)-mandelamide; m.p. 145°–147° C.; [alpha]= +26° (methanol, c=1%), identical with the product SR 58544 of Example 3 (c).

EXAMPLE 11

By operating as described in Example 10 and substituting the S(−)-2-amino-7-hydroxy-1,2,3,4tetrahydronaphtalene monohydrate (PREPARATION III) for the R(+)-2-amino-7-hydroxy-1,2,3,4-tetrahydronaphtalene monohydrate, there is obtained:
(a) N-[(2S)-7-hydroxy-1,2,3,4-tetrahydronapth-2-yl]-(RS)-mandelamide; mixture of diastereoisomers;
(b) N-[(2S)-7-hydroxy-1,2,3,4-tetrahydronaphth-2-yl]-(R or S)-mandelamide; m.p. 157°–159° C.; [alpha]= −107° (methanol, c=0.5%), identical with the product SR 58543 of Example 3(b);
(c) N-[(2S)-7-hydroxy-1,2,3,4-tetrahydronaphth-2-yl]-(S or R)-mandelamide, SR 58559; m.p. 147°–148° C.; [alpha]= −27.5° (methanol, c=0.5%).

EXAMPLE 12

To a solution of 3 g of N-[(2R)-7-hydroxy-1,2,3,4-tetrahydronaphth 2-yl]-(S)-3-chloromandelamide, SR 58588, described in Example 8(b), in 40 ml of anhydrous tetrahydrofuran, heated with reflux under nitrogen stream, there is added 2.7 ml of a 10M solution of boranemethylsulfide in 20 ml of tetrahydrofuran, and the refluxing is maintained for 4 hours. To the solution cooled to room temperature, there is added 25 ml of methanol and the reaction mixture is left under stirring at first at room temperature for 30 minutes and then at reflux for 30 minutes. The solution is concentrated under reduced pressure and, after filtration, the product is crystallized twice from isopropanol. There is obtained 2.1 g (73%) of N-[(2R)-7-hydroxy-1,2,3,4-tetrahydronaphth-2-yl]-(2S)-2-(3-chlorophenyl)-2-hydroxyethanamine, SR 58590; m.p. 186°–188° C.; [alpha]= +76° (methanol, c=0.5%).

EXAMPLE 13

By operating as described in Example 12, starting from 4.7 g of SR 58533, obtained as described in Example 8(c), a base is obtained as a residual oil that is purified by flash chromatography (elution with a 95/5 mixture of methylene chloride/methanol). The purified base is dissolved in acetone, the solution is filtered and a saturated solution of hydrogen chloride in isopropanol is added thereto. After filtration, the product is crystallized twice from isopropanol. The product is cooled, filtered and washed with isopropanol and, then, with acetone. There is obtained 3.2 g (65%) of N-[(2R)-7-hydroxy-1,2,3,4-tetrahydronaphth-2-yl]-(2R)-2-(3-chlorophenyl)-2-hydroxyethanamine hydrochloride, SR 58572 A; m.p. 203°–205° C.; [alpha]= +36.4° (methanol, c=1%).

EXAMPLE 14

By operating as described in Example 12, starting from 2.5 g of SR 58587, obtained as described in Example 9(b), there is obtained 1.6 g (67%) of N-[(2S)-7-hydroxy-1,2,3,4-tetrahydronaphth-2-yl]-(2R)-2-(3-chlorophenyl)-2-hydroxyethanamine, SR 58589; m.p. 185°-187° C.; [alpha]= −78.5° (methanol, c=0.5%).

EXAMPLE 15

By operating as described in Example 12 and using as starting product 3.44 g of SR 58574, obtained as described in Example 9(c), a base is obtained as an oil that is purified by flash chromatography (elution with a 95/5 mixture of methylene chloride/methanol). The purified base is dissolved in acetone, the solution is filtered and a saturated solution of hydrogen chloride in isopropanol is added thereto. After filtration, the product is crystallized twice from isopropanol. The product is cooled, filtered and washed with isopropanol and, then, with acetone to give 1.2 g (34%) of N-[(2S)-7-hydroxy-1,2,3,4-tetrahydronaphth-2-yl]-(2S)-2-(3-chlorophenyl)-2-hydroxyethanamine hydrochloride, SR 58575 A; m.p. 203°-205° C.; [alpha]= −35.8° (methanol, c=1%).

EXAMPLE 16

A solution of 2.4 g of N-[(2R)-7-hydroxy-1,2,3,4-tetrahydronaphth-2-yl]-(S or R)-mandelamide, SR 58561, obtained as described in Example 10(b), in 100 ml of tetrahydrofuran, is heated with reflux in the presence of 1.85 g of lithium aluminium hydride for 16 hours. After addition of a mixture of 5 ml of water in 13 ml of ethanol, the solution is stirred for 15 minutes, then concentrated ammonium hydroxide is added thereto. The product thus obtained is filtered and washed with ethanol. After evaporation to dryness, the residue is taken up with ethyl acetate. The resulting mixture is dried over anhydrous sodium sulfate and evaporated to dryness. After crystallization of the residue from 15 ml of isopropanol, there is obtained 1 g (44%) of N-[(2R)-7-hydroxy-1,2,3,4-tetrahydronaphth-2-yl]-(2S or 2R)-2-hydroxy-2-phenylethanamine, SR 58372; m.p. 172°-174° C.; [alpha]= +77.6° (DMF, c=1%).

EXAMPLE 17

By operating as described in Example 16 and using as starting product 2,3 g of SR 58544, obtained as described in Example 10(c), a base is obtained that is dissolved in 50 ml of acetone and the solution is made acid with a saturated solution of hydrogen chloride in ethanol. The product thus obtained is crystallized by dissolving it in 15 ml of isopropanol and by precipitation with 15 ml of ethyl ether. There is obtained 0.9 g (36%) of N-[(2R)-7-hydroxy-1,2,3,4-tetrahydronaphth-2-yl]-(2R or 2S)-2-hydroxy-2-phenylethanamine hydrochloride; m.p. 178°-180° C.; [alpha]= +40.3° (ethanol/eau 1/1, c=2%). This compound corresponds to the product SR 58375 A of Example 22 of EP 211721.

EXAMPLE 18

By operating as described in Example 16 and starting from 2.7 g of SR 58543, obtained as described in Example 11(b), there is obtained 1 g (40%) of N-[(2S)-7-hydroxy-1,2,3,4-tetrahydronaphth-2-yl]-(2R or 2S)-2-hydroxy-2-phenylethanamine, SR 58374; m.p. 173°-174° C.; [alpha]= −78.3° (DMF, c=1%).

EXAMPLE 19

By operating as described in Example 16, and starting from 3 g of SR 58559, obtained as described in Example 11(c), a base is obtained that is dissolved in 20 ml of acetone. The solution is made acid with a saturated solution of hydrogen chloride in isopropanol. The product thus obtained is crystallized by dissolving it in 8 ml of isopropanol and by precipitation with 8 ml of ethyl ether. There is obtained 1.55 g (49%) of N-[(2S)-7-hydroxy-1,2,3,4-tetrahydronaphth-2-yl]-(2S or 2R)-2-hydroxy-2-phenylethanamine hydrochloride; m.p. 179°-180° C.; [alpha]= −41.5° (ethanol/water 1/1, c=2%). This compound corresponds to the product SR 58373A of Example 23 of EP 211721.

EXAMPLE 20

To a suspension of 2.6 g of (R)-2-amino-7-hydroxytetralin hydrochloride (PREPARATION II), 2.4 g of (R)-3-chloromandelic acid (Bull. Soc. Chim. Fr., 1973, 12, 3330) and 5.2 g of BOP in 60 ml of anhydrous methylene chloride, there is added 3.6 ml of triethylamine slowly, then the solution thus obtained is stirred at room temperature for 3 hours. After addition of 50 ml of a saturated sodium chloride solution, the reaction mixture is stirred for 30 minutes at room temperature, then 200 ml of ethyl acetate are added thereto and the phases are separated. The organic phase is washed twice with 30 ml of a 2N hydrochloric acid solution, then twice with 30 ml of a saturated sodium chloride solution. The organic solution is dried over sodium sulfate, filtered and evaporated to dryness. The oil thus obtained is purified by flash chromatography (eluent 55/45 mixture of ethyl acetate/cyclohexane). A doughy solid is obtained that is taken up with 20 ml of ethyl ether from which the product crystallizes. After addition of 10 ml of cyclohexane, the solution is filtered, washed with a 2/1 mixture of cyclohexane/ethyl ether and dried under reduced pressure at 50° C. to give 2.4 g (55%) of a stereoisomer that is pure according to $^{13}$C RMN at 60 MHz; m.p. 132°-134° C., [alpha]= +24.9° (methanol, c=1%). In TLC this product has the same shift of the product of Example 1(c), SR 58536 (RR,SS) and no impurity corresponding to the Rf of SR 58535 (RS,SR) of Example 1(b) (elution with 1/1 ethyl acetate/cyclohexane). After a further purification by chromatography, there is obtained the enantiomerically and chemically pure N-[(2R)-7-hydroxy-1,2,3,4-tetrahydronaphth-2-yl]-(R)-3-chloromandelamide; m.p. 143°-147° C., [alpha]= +35.1° (methanol, c=1%). This product is identical with the compound SR 58533 of Example 8(c), the R,R configuration of which is thus confirmed.

EXAMPLE 21

By operating as described in Example 20 substituting the (S)-3-chloromandelic acid (Bull. Soc. Chim. Fr., 1973, 12, 3330) for the (R)-3-chloromandelic acid, the N-[(2R)-7-hydroxy-1,2,3,4-tetrahydronaphth-2-yl]-(S)-3-chloromandelamide is obtained as a solid having an undefined melting point; [alpha]= +92.5° (methanol, c=1%). This product is identical with the compound SR 58588 of Example 8(b), the (R,S) configuration of which is thus confirmed.

EXAMPLE 22

To a mixture of 3.6 g of (R)-3-chloromandelic acid, 3.5 g of S(−)-2-amino-7-hydroxy-1,2,3,4-tetrahydronaphtalene monohydrate (PREPARATION III)

and 7.7 g of BOP in 60 ml of anhydrous methylene chloride under nitrogen stream, there is added 2.7 ml of triethylamine. The solution obtained is stirred for 5 hours at room temperature, then 400 ml of ethyl acetate are added thereto and the organic phase is washed with water, separated and evaporated to dryness. The residue thus obtained is treated with 150 ml of N sodium hydroxide and extracted with ethyl ether. The organic phase is eliminated. The aqueous phase is acidified with concentrated hydrochloric acid and extracted with ethyl acetate. The organic phase thus obtained is washed with water, dried over sodium sulfate, filtered and evaporated to dryness. The oil thus obtained is purified by flash chromatography (elution with a 70/30 mixture of ethyl acetate/cyclohexane). An amount of 4 g (63%) of N-[(2S)-7-hydroxy-1,2,3,4-tetrahydronaphth-2-yl]-(R)-3-chloromandelamide is obtained as a very thick whittish oil that is treated with petroleum ether; a solid having an undefined melting point is obtained; [alpha]= −95° (methanol, c=1%). This product is identical with the compound SR 58587 of Example 9(b), the (S, R) configuration of which is thus confirmed.

EXAMPLE 23

By operating as described in Example 22 and substituting the (S)-3-chloromandelic acid for the (R)-3-chloromandelic acid, there is obtained the N-[(2S)-7-hydroxy-1,2,3,4-tetrahydronaphth-2-yl]-(S)-3-chloromandelamide; m.p. 145°–146° C.; [alpha]= −34.2° (methanol, c=1%). This product is identical with the compound SR 58574 of Example 9(c), the (S,S) configuration of which is thus confirmed.

EXAMPLE 24

By operating as described in Example 22 and replacing the (R)-3-chloromandelic acid by an equimolecular amount of (R)-mandelic acid there is obtained the N-[(2S)-7-hydroxy-1,2,3,4-tetrahydronaphth-2-yl]-(R)-mandelamide; m.p. 159°–160° C.; [alpha]= −113° (methanol, c=0.5%). This product is identical with the compound SR 58543 of Examples 3(b) and 11(b), the (S, R) configuration of which is thus defined.

EXAMPLE 25

By operating as described in Example 22 and replacing the (R)-3-chloromandelic acid by an equimolecular amount of (S)-mandelic acid, there is obtained the N-[(2S)-7-hydroxy-1,2,3,4-tetrahydronaphth-2-yl]-(S)-mandelamide; m.p. 147°–148° C.; [alpha]= −27.5° (methanol, c=0.5%). This product is identical with the compound SR 58559 of Example 11(c), to which the (S,S) configuration is thus finally assigned.

EXAMPLE 26

By operating as described in Example 22 and replacing the (R)-3-chloromandelic acid by an equimolecular amount of (R)-mandelic acid and the S(−)-2-amino-7-hydroxy-1,2,3,4-tetrahydronaphtalene monohydrate by the R(+)-2-amino-7-hydroxy-1,2,3,4-tetrahydronaphtalene monohydrate, there is obtained the N-[(2R)-7-hydroxy-1,2,3,4-tetrahydronaphth-2-yl]-(R)-mandelamide; m.p. 145°–147° C.; [alpha]= +26° (methanol, c=1%). This product is identical with the compound SR 58544 of Examples 3(c) and 10(c), to which the (R,R) configuration is thus finally assigned.

EXAMPLE 27

By operating as described in Example 22 and replacing the (R)-3-chloromandelic acid by an equimolecular amount of (S)-mandelic acid and the S(−)-2-amino-7-hydroxy-1,2,3,4-tetrahydronaphtalene monohydrate by the R(+)-2-amino-7-hydroxy-1,2,3,4-tetrahydronaphtalene monohydrate, there is obtained the N-[(2R)-7-hydroxy-1,2,3,4-tetrahydronaphth-2-yl]-(S)-mandelamide; m.p. 159°–160° C.; [alpha]= +110° (methanol, c=0.5%). This product is identical with the compound SR 58561 of Example 10(b), the (R, S) configuration of which is thus defined.

EXAMPLES 28 A 31

By submitting the products of Examples 20 to 23 to a reduction with borane-methylsulfide as described in Example 12, the following products are obtained:

-N-[(2R)-7-hydroxy-1,2,3,4-tetrahydronaphth-2-yl]-(2R)-2-(3-chlorophenyl)-2-hydroxyethanamine hydrochloride, identical with compound SR 58572 A of Example 13, the (R,R) configuration of which is confirmed (Example 28);

-N-[(2R)-7-hydroxy-1,2,3,4-tetrahydronaphth-2-yl]-(2S)-2-(3-chlorophenyl)-2-hydroxyethanamine, identical with compound SR 58590 of Example 12, the (R, S) configuration of which is thus confirmed (Example 29);

-N-[(2S)-7-hydroxy-1,2,3,4-tetrahydronaphth-2-yl]-(2R)-2-(3-chlorophenyl)-2-hydroxyethanamine, identical with compound SR 58589 of Example 14, the (S, R) configuration of which is thus confirmed (Example 30);

-N-[(2S)-7-hydroxy-1,2,3,4-tetrahydronaphth-2-yl]-(2S)-2-(3-chlorophenyl)-2-hydroxyethanamine hydrochloride, identical with compound SR 58575A of Example 15, the (S,S) configuration of which is thus confirmed (Example 31).

EXAMPLES 32 A 35

By submitting the products of Examples 24 to 27 to a reduction with lithium and aluminium hydride as described in Example 16, the following products are obtained:

-N-[(2S)-7-hydroxy-1,2,3,4-tetrahydronaphth-2-yl]-(2R)-2-hydroxy-2-phenylethanamine, identical with compound SR 58374 of Example 18, the (S, R) configuration of which is thus defined (Example 32);

-N-[(2R)-7-hydroxy-1,2,3,4-tetrahydronaphth-2-yl]-(2R)-2-hydroxy-2-phenylethanamine hydrochloride, identical with compound SR 58375 A of Example 17 the (R, S) configuration of which is thus defined (Example 33)

-N-[(2S)-7-hydroxy-1,2,3,4-tetrahydronaphth-2-yl]-(2S)-2-hydroxy-2-phenylethanamine hydrochloride, identical with compound SR 58373 A of Example 19, to which the (S,S) configuration is finally assigned (Example 34);

-N-[(2R)-7-hydroxy-1,2,3,4-tetrahydronaphth-2-yl]-(2S)-2-hydroxy-2-phenylethanamine, identical with compound SR 58372 of Example 16, the (R, S) configuration of which is thus defined (Example 35).

EXAMPLE 36

A mixture of 15.8 g of N-[(2S)-7-hydroxy-1,2,3,4-tetrahydronaphth-2-yl]-(R)-mandelamide, obtained according to Example 3(b), 7.1 ml of ethyl bromoacetate, 22 g of anhydrous potassium carbonate and 1 g of potassium iodide in 600 ml of anhydrous acetone, is heated with reflux and with stirring for 5 hours and a half. The reaction mixture is filtered, evaporated to dryness and the oil which separates is left to crystallize. The solid so obtained is purified by flash-chromatography (elution with a 1/1 mixture of ethyl acetate/cyclohexane). The solid on the column is taken up and treated with 20 ml of ethyl ether, filtered and crystallized from ethyl acetate to give 11.5 g of N-[(2S)-7-carbethoxymethoxy-1,2,3,4-tetrahydronaphth-2-yl]-(R)-mandelamide, SR 58638; m.p. 115°-117° C.; [alpha]=−98.3° (methanol, c=1%). Yield: 57%.

EXAMPLE 37

To a solution of 5 g of N-[(2S)-7-carbethoxymethoxy-1,2,3,4-tetrahydronaphth-2-yl]-(R)-mandelamide, Example 36, in 50 ml of anhydrous tetrahydrofuran, there is added, dropwise, 2.6 ml of a 10M solution of borane-methylsulfide in 10 ml of anhydrous tetrahydrofuran under nitrogen stream at 0° C. temperature over a period of 10 minutes and the reaction mixture is left to stand at room temperature overnight. The borane-methylsulfide that has not reacted is destroided by a cautious addition of 30 ml of absolute ethanol and by heating with reflux for 30 minutes. The solution is evaporated to dryness and submitted to a flash chromatography (elution with a 85/15 mixture of ethyl acetate/methanol). There are obtained two products that are taken up with ethyl ether.

The less polar product, after crystallization from ethyl acetate, gives 1.2 g of N-[(2S)-7-carbethoxymethoxy-1,2,3,4-tetrahydronaphth-2-yl]-(2R)-2-hydroxy-2-phenylethanamine, SR 58639; m.p. 108°-111° C.; [alpha]=−78.65° (methanol, c=1%).

The yield of SR 58639 is 25.2%. The global yield starting from N-[(2S)-7-hydroxy-1,2,3,4-tetrahydronaphth-2-yl]-(R)-mandelamide is 14.36%.

The more polar product, after crystallization from ethyl acetate, gives 0.5 g of N-[(2S)-7-(2-hydroxyethoxy-1,2,3,4-tetrahydronaphth-2-yl]-(2R)-2-hydroxy-2-phenylethanamine, SR 58640; m.p. 94°-96° C.; [alpha]=−83.68° (methanol, c=1%).

EXAMPLE 38

By operating as described in Example 37, and using the same quantities of reagents, but heating with reflux for 3 hours, there is obtained:

0.8 g of N-[(2S)-7-carbethoxymethoxy-1,2,3,4-tetrahydronaphth-2-yl]-(2R)-2-hydroxy-2-phenylethanamine, SR 58639, and 1.8 g of N-[(2S)-7-(2-hydroxyethoxy)-1,2,3,4-tetrahydronaphth-2-yl]-(2R)-2-hydroxy-2-phenylethanamine, SR 58640, identical with the compounds of Example 37.

The latter compound, SR 58640, has a good activity on the intestinal motility in the rat isolated colon test (EP 255 415).

We claim:

1. A process for the preparation of phenylethanolaminotetralins of formula

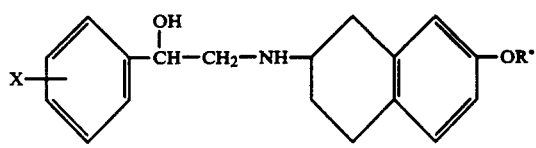

wherein X is hydrogen, a halogen, a trifluoromethyl group or a lower alkyl group and R° is hydrogen or a methyl group substituted by a carboxy or lower carbalkoxy group; and of their pharmaceutically acceptable salts, which comprises treating a functional derivative of a mandelic acid of formula

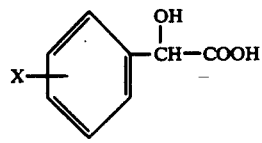

wherein X is as defined hereinabove, with an aminotetralin of formula

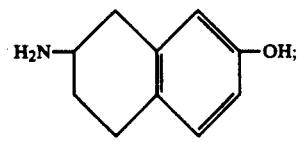

the mandelamine thus obtained of formula

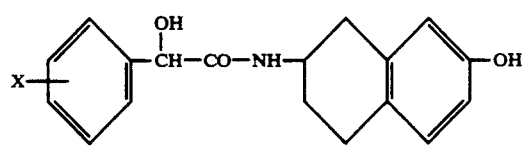

wherein X is as defined hereinabove, is then, submitted to a reduction for the transformation of the amido group into the methyleneamino group or alternatively treated with a lower alkyl haloacetate in the presence of a basic condensation agent, the above mentioned haloacetate being a bromo-, chloro- or iodoacetate; on this second assumption submitting the resulting product, in any order to a reduction for the transformation of the amido group into a methylene amino group and, if desired, to a saponification of the lower carbalkoxy group into the carboxy group; and, if desired, transforming the product thus obtained into one of its pharmaceutically acceptables salts.

2. A process according to claim 1 in which a mandelic acid in its (R) configuration is used as starting product.

3. A process according to claim 1 in which (R)-3-chloromandelic acid is used as starting product.

4. A process according to claim 1 in which racemic 3-chloromandelic acid is used as starting product.

5. A process according to claim 1 in which the free acid, activated by hexafluorophosphate of benzotriazolyl-N-oxytris(dimethylamino)phosphonium is used as functional derivative of the starting mandelic acid.

6. A process according to claim 1 in which a racemic 2-amino-7-hydroxy-1,2,3,4,tetrahydronaphthalene is used as starting aminotetralin.

7. A process according to claim 1 in which the (S)-2-amino-7-hydroxy-1,2,3,4-tetrahydronaphthalene is used as starting aminotetralin.

8. The process of claim 1 which further comprises, when the amide (IV) is obtained as a mixture of isomers, separating it into the single diastereoisomers or diastereoisomeric couples of enantiomers, by chromatography.

9. The process of claim 8 wherein one of the starting compounds of formula (II) and (III) is used in optically active form.

* * * * *